US008636462B2

(12) United States Patent
Kraemer et al.

(10) Patent No.: US 8,636,462 B2
(45) Date of Patent: Jan. 28, 2014

(54) METHODS, SYSTEMS AND APPARATUS FOR DETECTING MATERIAL DEFECTS IN ROTOR BLADES OF COMBUSTION TURBINE ENGINES

(75) Inventors: Gilbert Otto Kraemer, Greer, SC (US); Dullal Ghosh, Orissa (IN); Bhaskara Rao Atchuta, Karnataka (IN)

(73) Assignee: General Electric Company, Schenectady, NY (US)

( * ) Notice: Subject to any disclaimer, the term of this patent is extended or adjusted under 35 U.S.C. 154(b) by 581 days.

(21) Appl. No.: 12/987,365

(22) Filed: Jan. 10, 2011

(65) Prior Publication Data

US 2012/0177491 A1 Jul. 12, 2012

(51) Int. Cl.
*F01D 21/10* (2006.01)
*F01D 25/00* (2006.01)

(52) U.S. Cl.
USPC ....... 415/1; 415/118; 416/1; 416/61; 324/700

(58) Field of Classification Search
USPC ...................... 415/1, 118; 416/1, 61; 324/700
See application file for complete search history.

(56) References Cited

U.S. PATENT DOCUMENTS

| | | | |
|---|---|---|---|
| 4,380,172 A | 4/1983 | Imam et al. | |
| 4,573,123 A | 2/1986 | Rosenbush et al. | |
| 5,594,665 A * | 1/1997 | Walter et al. | 415/26 |
| 6,014,896 A | 1/2000 | Schoess | |
| 6,278,374 B1 | 8/2001 | Ganeshan | |
| 6,512,379 B2 | 1/2003 | Harrold et al. | |
| 6,756,908 B2 | 6/2004 | Gass et al. | |
| 7,123,031 B2 | 10/2006 | Twerdochlib | |
| 8,475,110 B2 * | 7/2013 | Hefner et al. | 415/1 |
| 2002/0116985 A1 | 8/2002 | Henning et al. | |
| 2004/0056654 A1 | 3/2004 | Goldfine et al. | |
| 2007/0258807 A1 | 11/2007 | Brummel | |

OTHER PUBLICATIONS

Search Report and Written Opinion from FR Application No. 1250252 dated Jun. 4, 2013.

* cited by examiner

*Primary Examiner* — Igor Kershteyn
(74) *Attorney, Agent, or Firm* — Mark E. Henderson; Ernest G. Cusick; Frank A. Landgraff (57) ABSTRACT

A system for detecting defects in a turbine rotor blade of a combustion turbine engine. The system may include: a turbine rotor blade that includes an insulator coating; a first electrode that is electrically connected to the turbine rotor blade; a second electrode that resides in proximity to the turbine rotor blade; means for inducing a voltage across the first electrode and the second electrode; and means for detecting current flowing between the first electrode and the second electrode.

22 Claims, 5 Drawing Sheets

METHODS, SYSTEMS AND APPARATUS FOR DETECTING MATERIAL DEFECTS IN ROTOR BLADES OF COMBUSTION TURBINE ENGINES

BACKGROUND OF THE INVENTION

This present application relates generally to methods, systems, and apparatus for detecting defects, including surface defects, that may occur in industrial manufacturing processes, engines, or similar systems. More specifically, but not by way of limitation, the present application relates to methods, systems, and apparatus pertaining to the detection of defects that form on the components, such as turbine rotor blades, exposed to the hot-gas path of combustion turbine engines.

In operation, generally, a combustion turbine engine may combust a fuel with compressed air supplied by a compressor. As used herein and unless specifically stated otherwise, a combustion turbine engine is meant to include all types of turbine or rotary combustion engines, including gas turbine engines, aircraft engines, etc. The resulting flow of hot gases, which typically is referred to as the working fluid, is expanded through the turbine section of the engine. The interaction of the working fluid with the rotor blades of the turbine section induces rotation in the turbine shaft. In this manner, the energy contained in the fuel is converted into the mechanical energy of the rotating shaft, which, for example, then may be used to rotate the rotor blades of the compressor, such that the supply of compressed air needed for combustion is produced, and the coils of a generator, such that electrical power is generated. During operation, it will be appreciated that components exposed to the hot-gas path become highly stressed with extreme mechanical and thermal loads. This is due to the extreme temperatures and velocity of the working fluid, as well as the rotational velocity of the turbine. As higher firing temperatures correspond to more efficient heat engines, technology is ever pushing the limits of the materials used in these applications.

Whether due to extreme temperature, mechanical loading or combination of both, component failure remains a significant concern in combustion turbine engines. A majority of failures can be traced to material fatigue, which typically is forewarned by the onset of crack propagation. More specifically, the formation of cracks caused by material fatigue remains a primary indicator that a component has reached the limit of its useful life and may be nearing failure. This is particularly true for rotating components such as turbine rotor blades. As a result, the ability to detect the formation of cracks remains an important industry objective, particularly when considering the catastrophic damage that the failure of a single component—such as a turbine rotor blade—may occasion. Such a failure event may cause a chain reaction that destroys downstream systems and components, which require expensive repairs and long outages.

One manner in which the useful life of hot-gas path components may be extended is through the use of protective coatings, such as thermal barrier coatings. In general, exposed surfaces are covered with these coatings, and the coatings insulate the component against the most extreme temperatures of the hot-gas path. However, as one of ordinary skill in the art will appreciate, these types of coatings wear or fragment during usage, a process that is typically referred to as "coating spallation" or "spallation". Spallation may result in the formation and growth of uncoated or exposed areas at discrete areas or patches on the surface of the affected component. These unprotected areas experience higher temperatures and, thus, are subject to more rapid deterioration, including the premature formation of fatigue cracks and other defects. In combustion turbine engines, coating spallation is a particular concern for turbine rotor blades and components within the combustor, such as the transition piece. Early detection of coating spallation may allow an operator to take corrective action before the component becomes completely damaged from the increased thermal strain.

While the operators of combustion turbine engines want to avoid using worn-out or compromised components that risk failing during operation, they also have a competing interests of not prematurely replacing components before their useful life is exhausted. That is, operators want to exhaust the useful life of each component, thereby minimizing part costs while also reducing the frequency of engine outages for part replacements to occur. Accordingly, accurate crack detection and/or coating spallation in engine components is a significant industry need. However, conventional methods generally require regular visual inspection of parts. While useful, visual inspection is both time-consuming and requires the engine be shutdown for a prolonged period.

The ability to monitor components in the hot-gas path while the engine operates for the formation of cracks and the spallation of protective coatings remains a longstanding need. What is needed is a system by which crack formation and spallation may be monitored while the engine operates so that necessary action may be taken before a failure event occurs or significant component damage is realized. Such a system also may extend the life of components as the need for part replacement may be based on actual, measured wear instead of what is anticipated. In addition, such a system would decrease the need or frequency of performing evaluations, such as visual inspections, that require engine shutdown. To the extent that these objectives may be achieved in a cost-effective manner, efficiency would be enhanced and industry demand would be high.

BRIEF DESCRIPTION OF THE INVENTION

The present invention, thus, describes a system for detecting defects in a turbine rotor blade of a combustion turbine engine while the engine operates. In one embodiment, the system includes: a turbine rotor blade that includes an insulator coating; a first electrode that is electrically connected to the turbine rotor blade; a second electrode that resides in proximity to the turbine rotor blade; means for inducing a voltage across the first electrode and the second electrode; and means for detecting current flowing between the first electrode and the second electrode.

The present invention further describes a method for detecting defects in a turbine rotor blade of a combustion turbine engine while the combustion turbine engine is operating. In one embodiment the method includes the steps of: providing a first electrode that is electrically connected to the turbine rotor blade; providing a second electrode that resides in proximity to the turbine rotor blade; applying a voltage across the first electrode and the second electrode; and detecting current flowing between the first electrode and the second electrode.

These and other features of the present application will become apparent upon review of the following detailed description of the preferred embodiments when taken in conjunction with the drawings and the appended claims.

BRIEF DESCRIPTION OF THE DRAWINGS

These and other features of this invention will be more completely understood and appreciated by careful study of the following more detailed description of exemplary embodiments of the invention taken in conjunction with the accompanying drawings, in which.

DETAILED DESCRIPTION OF THE INVENTION

Figure 1:
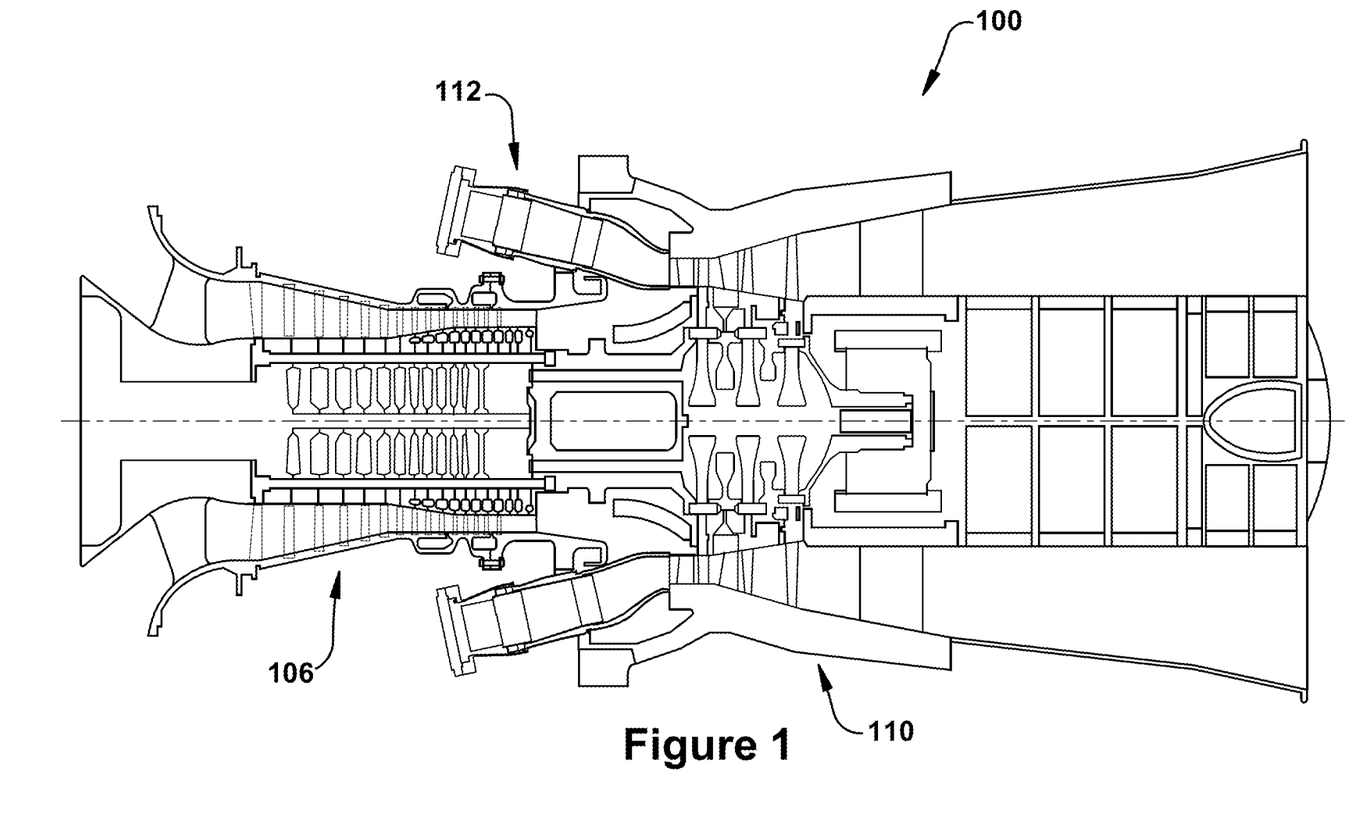
FIG. 1 illustrates a schematic representation of an exemplary combustion turbine engine in which embodiments of the present application may be used.

Referring now to the figures, FIG. 1 illustrates a schematic representation of a combustion or gas turbine engine 100 in which embodiments of the present invention may be employed. In general, gas turbine engines operate by extracting energy from a pressurized flow of hot gas that is produced by the combustion of a fuel in a stream of compressed air. As illustrated in FIG. 1, gas turbine engine 100 may be configured with an axial compressor 106 that is mechanically coupled by a common shaft or rotor to a downstream turbine section or turbine 110, and a combustion system 112, which, as shown, is a can combustor that is positioned between the compressor 106 and the turbine 110.

Figure 2:
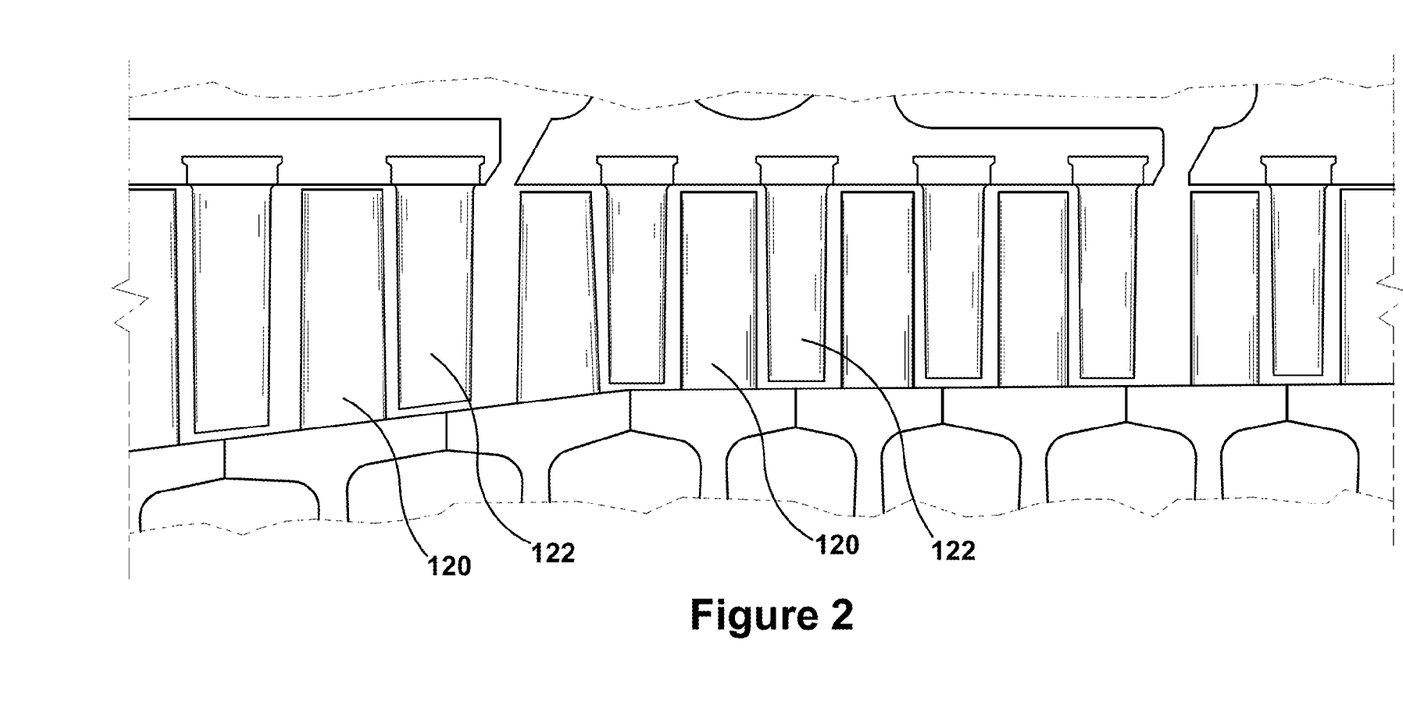
FIG. 2 illustrates a sectional view of an exemplary compressor that may be used in the gas turbine engine of FIG. 1.

FIG. 2 illustrates a view of an axial compressor 106 that may be used in gas turbine engine 100. As shown, the compressor 106 may include a plurality of stages. Each stage may include a row of compressor rotor blades 120 followed by a row of compressor stator blades 122. Thus, a first stage may include a row of compressor rotor blades 120, which rotate about a central shaft, followed by a row of compressor stator blades 122, which remain stationary during operation. The compressor stator blades 122 generally are circumferentially spaced one from the other and fixed about the axis of rotation. The compressor rotor blades 120 are circumferentially spaced about the axis of the rotor and rotate about the shaft during operation. As one of ordinary skill in the art will appreciate, the compressor rotor blades 120 are configured such that, when spun about the shaft, they impart kinetic energy to the air or working fluid flowing through the compressor 106. As one of ordinary skill in the art will appreciate, the compressor 106 may have many other stages beyond the stages that are illustrated in FIG. 2. Each additional stage may include a plurality of circumferential spaced compressor rotor blades 120 followed by a plurality of circumferentially spaced compressor stator blades 122.

Figure 3:
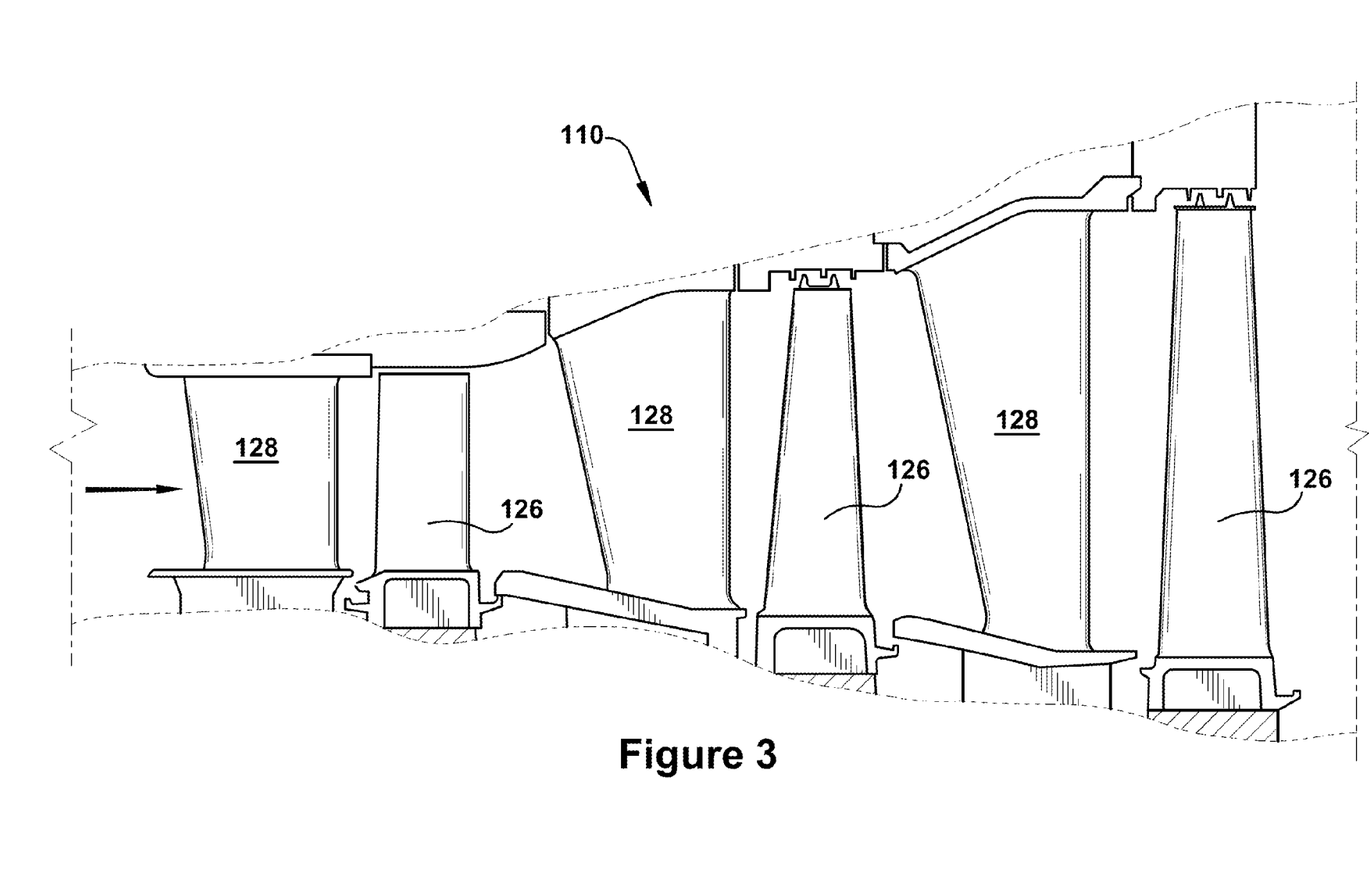
FIG. 3 illustrates a sectional view of an exemplary turbine that may be used in the combustion turbine engine of FIG. 1.
Figure 4:
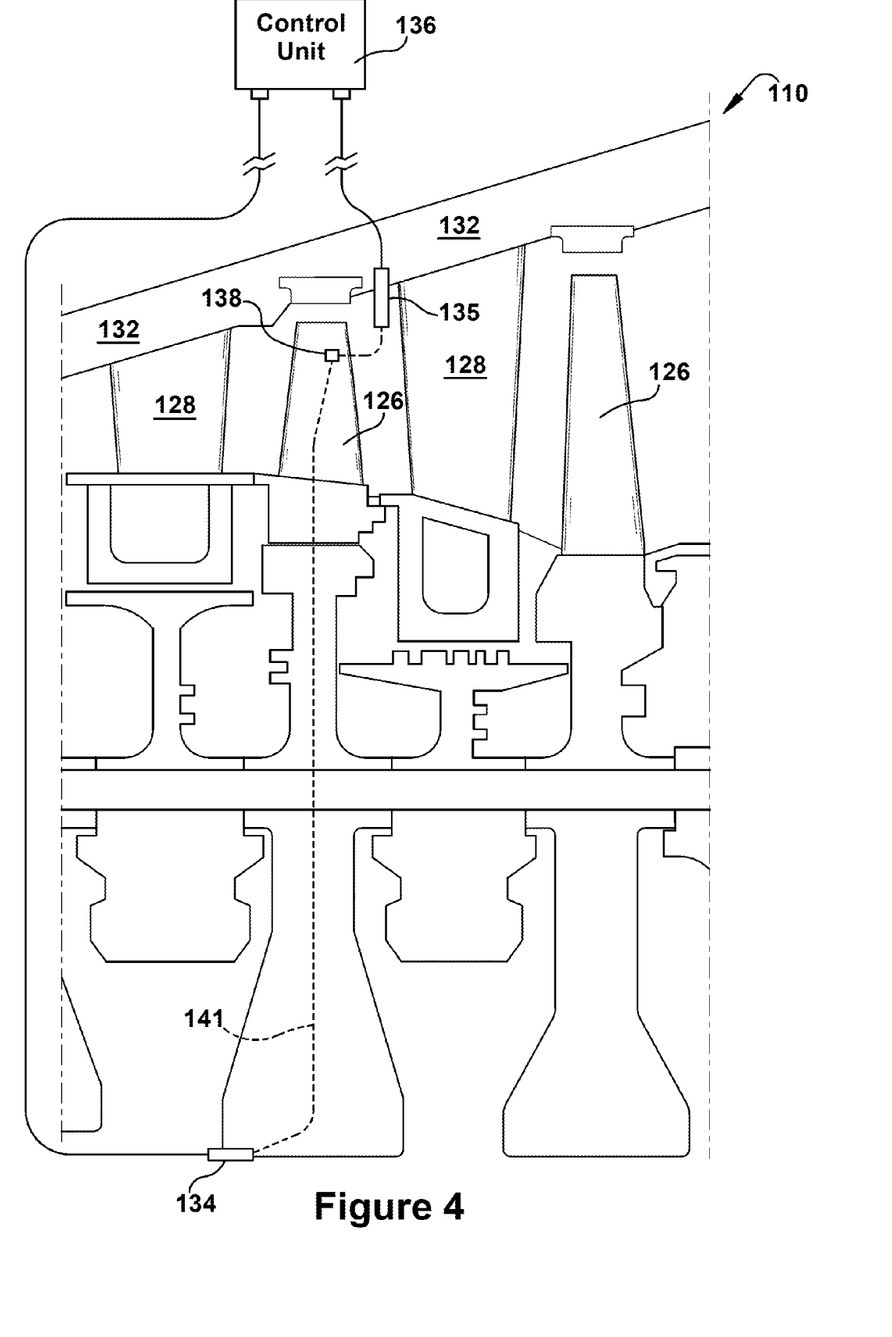
FIG. 4 illustrates a sectional view of an exemplary turbine and a system in accordance with an exemplary embodiment of the present application.

FIG. 3 illustrates a partial view of an exemplary turbine section or turbine 110 that may be used in a gas turbine engine 100. The turbine 110 may include a plurality of stages. Three exemplary stages are illustrated, but more or less stages may be present in the turbine 110. A first stage includes a plurality of turbine buckets or turbine rotor blades 126, which rotate about the shaft during operation, and a plurality of nozzles or turbine stator blades 128, which remain stationary during operation. The turbine stator blades 128 generally are circumferentially spaced one from the other and fixed about the axis of rotation. The turbine rotor blades 126 may be mounted on a turbine wheel 130 (as indicated in FIG. 4) for rotation about the shaft. A second stage of the turbine 110 is also illustrated. The second stage similarly includes a plurality of circumferentially spaced turbine stator blades 128 followed by a plurality of circumferentially spaced turbine rotor blades 126, which are also mounted on a turbine wheel for rotation. A third stage also is illustrated, and similarly includes a plurality of circumferentially spaced turbine stator blades 128 and turbine rotor blades 126. It will be appreciated that the turbine stator blades 128 and turbine rotor blades 126 lie in the hot gas path of the turbine 110. The direction of flow of the hot gases through the hot gas path is indicated by the arrow. As one of ordinary skill in the art will appreciate, the turbine 110 may have many other stages beyond the stages that are illustrated in FIG. 3. Each additional stage may include a plurality of circumferential spaced turbine stator blades 128 followed by a plurality of circumferentially spaced turbine rotor blades 126.

A gas turbine engine of the nature described above may operate as follows. The rotation of compressor rotor blades 120 within the axial compressor 106 compresses a flow of air. In the combustor 112, as described in more detail below, energy is released when the compressed air is mixed with a fuel and ignited. The resulting flow of hot gases from the combustor 112 then may be directed over the turbine rotor blades 126, which may induce the rotation of the turbine rotor blades 126 about the shaft, thus transforming the energy of the hot flow of gases into the mechanical energy of the rotating shaft. The mechanical energy of the shaft may then be used to drive the rotation of the compressor rotor blades 120, such that the necessary supply of compressed air is produced, and also, for example, a generator to produce electricity.

Before proceeding further, it will be appreciated that in order to communicate clearly the present invention, it will become necessary to select terminology that refers to and describes certain parts or machine components of a turbine engine and related systems, particularly, the combustor system. Whenever possible, industry terminology will be used and employed in a manner consistent with its accepted meaning. However, it is meant that any such terminology be given a broad meaning and not narrowly construed such that the meaning intended herein and the scope of the appended claims is unreasonably restricted. Those of ordinary skill in the art will appreciate that often a particular component may be referred to using several different terms. In addition, what may be described herein as a single part may include and be referenced in another context as consisting of several component parts, or, what may be described herein as including multiple component parts may be fashioned into and, in some cases, referred to as a single part. As such, in understanding the scope of the invention described herein, attention should not only be paid to the terminology and description provided, but also to the structure, configuration, function, and/or usage of the component, as provided herein.

In addition, several descriptive terms may be used regularly herein, and it may be helpful to define these terms at this point. These terms and their definition given their usage herein is as follows. The term "rotor blade", without further specificity, is a reference to the rotating blades of either the compressor or the turbine, which include both compressor rotor blades and turbine rotor blades. The term "stator blade", without further specificity, is a reference the stationary blades of either the compressor or the turbine, which include both compressor stator blades and turbine stator blades. The term "blades" will be used herein to refer to either type of blade. Thus, without further specificity, the term "blades" is inclusive to all type of turbine engine blades, including compressor rotor blades, compressor stator blades, turbine rotor blades, and turbine stator blades. Further, as used herein, "downstream" and "upstream" are terms that indicate a direction relative to the flow of a fluid, such as the working fluid through the turbine. As such, the term "downstream" refers to a direction that generally corresponds to the direction of the flow of working fluid, and the term "upstream" generally refers to the direction that is opposite of the direction of flow of working fluid. The terms "forward" or "leading" and "aft" or "trailing" generally refer to relative position in relation to the forward end and aft end of the turbine engine (i.e., the compressor is the forward end of the engine and the end having the turbine is the aft end). At times, which will be clear given the description, the terms "leading" and "trailing" may refer to the direction of rotation for rotating parts. When this is the case, the "leading edge" of a rotating part is the edge that leads in the rotation and the "trailing edge" is the edge that trails.

The term "radial" refers to movement or position perpendicular to an axis. It is often required to described parts that are at differing radial positions with regard to an axis. In this case, if a first component resides closer to the axis than a second component, it may be stated herein that the first component is "radially inward" or "inboard" of the second component. If, on the other hand, the first component resides further from the axis than the second component, it may be stated herein that the first component is "radially outward" or "outboard" of the second component. The term "axial" refers to movement or position parallel to an axis. Finally, the terms "circumferential" or "angular position" refers to movement or position around an axis.

Figure 5:
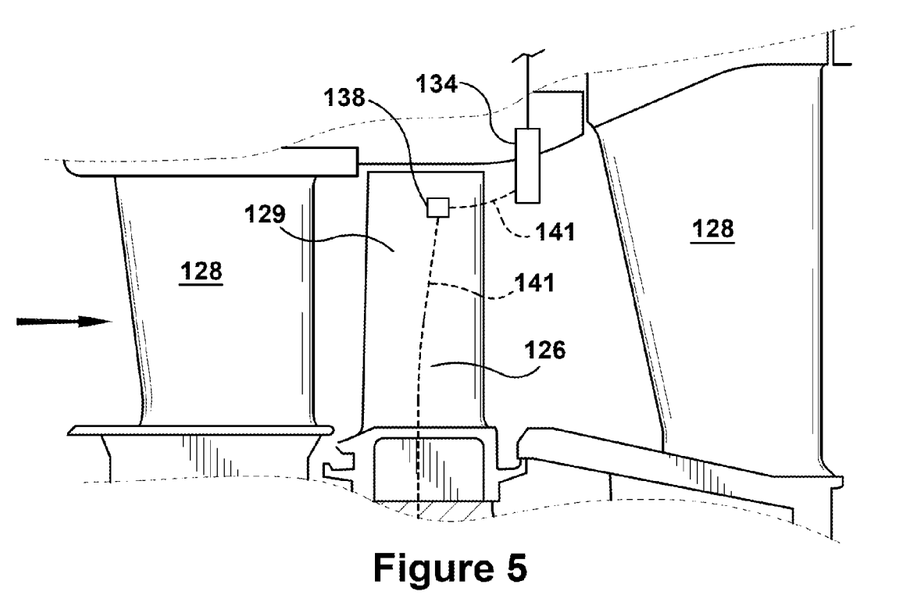
FIG. 5 illustrates a sectional view of an exemplary turbine and a system for monitoring material defects in accordance with an exemplary embodiment of the present application.

Referring to FIGS. 4 and 5, exemplary embodiments of the present invention are provided. According to an exemplary embodiment of the present invention, the turbine rotor blades 126 may be coated with an insulator coating 129. In some embodiments, the insulator coating 129 may comprise a thermal barrier coating. In particular, a zirconia oxide thermal barrier coating may be used in certain preferred environments. However, the present invention is not limited to this type of coating. Any coating that is suitable for use in the turbine environment and proves to be less electrically conductive as the underlying structure of the rotor blade 126 may be used.

The outer perimeter of the flow path of the turbine 110, as shown, may be enclosed by a turbine casing or casing 132. A first electrode 134 may be electrically connected to the row of turbine rotor blades 126. For example, the connection may be made to via conventional slip rings to a component such as the rotor wheel or directly to a static part such as a bearing surface. A second electrode 135 may be positioned on stationary structure in proximity to the row of turbine rotor blades 126 to which the first electrode 134 is attached. The second electrode 135 may be positioned, at least in part, within the hot-gas flow path. In an exemplary embodiment, as shown, the second electrode 135 is attached to the casing 132 just downstream of the row of rotor blades 126. The second electrode 135 may be constructed of materials capable of withstanding the rigors of the hot-gas flow path. For example, the second electrode 135 may comprise copper, silver, manganese, silicon or other suitable materials. The first electrode 134 and the second electrode 135, as indicated in FIG. 4, may be connected to a control unit 136. The control unit 136 may include a voltage source that is configured to apply a voltage across the two electrodes 134, 135. The voltage source may include any conventional systems having a voltage supply. The control unit 136 may include an amp meter or similar instrumentation for determining if current flows between the two electrodes 134, 135 and/or the level of current flowing between the two electrodes 134, 135.

During normal operation, it will be appreciated that the control unit 136 will observe no or comparatively little current flowing between the two electrodes 134, 135. This is due to the insulator coating 129 that covers and electrically insulates the rotor blades 126. However, when a crack originates at any location on the rotor blades 126, it may undermine the insulator coating 129 and eventually cause a weak location in the coating such that a defect 138 forms, which exposes a patch or portion of metallic surface of the turbine rotor blade 126 to the hot gases of the hot-gas flow path. It will be appreciated by those of ordinary skill in the art that the hot gases are electrically conducting and that a circuit 141 may be formed therethrough. As such, the control unit 136 or amp meter will detect that current is flowing between the two electrodes 134, 135 and that the electric circuit 141 has formed. In exemplary embodiments, the detection of the circuit 141 may cause the system to provide a warning notification that a defect 138 is likely and/or that corrective action should be taken. The sensitivity of the system may be adjusted by using different voltages or requiring certain predetermined current thresholds be satisfied before a warning notification is issued. It will be appreciated that such current thresholds may be configured to correspond with a defect of a certain size (i.e., the exposure of a certain amount of the more-conductive surface area of the rotor blade).

In an alternative embodiment, a current may be observed as flowing between the two electrodes 134, 135 during normal operation, which then becomes elevated when a defect is detected. This may be due to the fact that certain types of protective insulator coatings are electrically conductive (or, at least, more electrically conductive than other types of coatings). Accordingly, in this case, during normal operation, it will be appreciated that there may be a level of current observed by the control unit 136 between the two electrodes 134, 135. However, when a crack originates that exposes a patch or portion of the more electrically conductive surface of the turbine rotor blade 126 to the hot gases of the flowpath, an increased level of current flowing between the two electrodes 134, 135 will be observed by the control unit 136. In this embodiment, the observation of the increase in electrical current provides the warning signal for a defect 138. As before, the detection of the increased current through circuit 141 may cause the system to provide a warning notification that a defect 138 is likely and/or that corrective action should be taken. The sensitivity of the system may be adjusted by using different voltages or requiring certain current thresholds, or thresholds indicating a certain level of current change, be satisfied before a warning notification is issued.

In some embodiments, the conductivity of the hot gases of the flow path may be significantly increased by doping the fuel with a conducting material or injecting a conducting media in to the flowpath of compressed air. In some embodiments, this may be done periodically during test cycles in which tests for defects (i.e., crack formation or coating spallation) are performed. In addition, the size of the defect 138 may be determined by calibrating the system with the magnitude of current flow through the formed electrical circuit 141 given the voltage applied and prior defect sizes as well as other relevant conditions (i.e., whether a doping agent is present, etc.). For example, higher current levels will be indicative of bigger defect sizes. And, lower current levels that do not rise beyond a threshold current level may indicate the rotor blades are substantially defect free.

In the absence of crack formation, the erosion or spallation of the electrical insulting coating also may cause a defect 138 that exposes the metallic surface of the rotor blade 126 to the hot gases of the flow path. This also may lead to the formation of the electrical circuit between the two electrodes 134, 135 and cause the detection of the indicator current by the control unit 136. The spallation may be caused by the wearing away or erosion of the insulator coating of the rotor blades 126. In this case, the system may prevent the formation of cracks (as well as oxidation of the rotor blade) by warning of coating spallation that would, absent corrective action, cause greater thermal strain to the rotor blades 126.

It will be appreciated that monitoring crack formation and coating spallation while the engine operates may reduce the need for regular visual inspections, which may also reduce engine down time. In addition, monitoring while the engine operates may detect the formation of a significant defect that otherwise would have gone noticed until the next scheduled inspection. In this case, a catastrophic failure event may be avoided.

As one of ordinary skill in the art will appreciate, the many varying features and configurations described above in relation to the several exemplary embodiments may be further selectively applied to form the other possible embodiments of the present invention. For the sake of brevity and taking into account the abilities of one of ordinary skill in the art, all of the possible iterations is not provided or discussed in detail, though all combinations and possible embodiments embraced by the several claims below or otherwise are intended to be part of the instant application. In addition, from the above description of several exemplary embodiments of the invention, those skilled in the art will perceive improvements, changes and modifications. Such improvements, changes and modifications within the skill of the art are also intended to be covered by the appended claims. Further, it should be apparent that the foregoing relates only to the described embodiments of the present application and that numerous changes and modifications may be made herein without departing from the spirit and scope of the application as defined by the following claims and the equivalents thereof.

We claim:

1. A system for detecting defects in a turbine rotor blade of a combustion turbine engine while the combustion turbine engine operates, the system comprising:
    a turbine rotor blade that includes an insulator coating;
    a first electrode that is electrically connected to the turbine rotor blade;
    a second electrode that resides in proximity to the turbine rotor blade;
    means for inducing a voltage across the first electrode and the second electrode; and
    means for detecting current flowing between the first electrode and the second electrode.

2. The system according to claim 1, wherein the first electrode is connected to a rotor wheel into which the turbine rotor blade is attached;
    wherein the connection of the first electrode to the rotor wheel comprises one of: a) a slip ring connection to a rotating part; and b) a connection to a non-rotating bearing surface; and
    wherein the second electrode is connected to a turbine casing.

3. The system according to claim 1, wherein the second electrode is connected to stationary structure just downstream of a row of turbine blades in which the turbine rotor blade is included;
    wherein the second electrode is exposed to the hot-gas flowpath of the combustion turbine engine; and
    wherein the insulator coating comprises a thermal barrier coating.

4. The system according to claim 1, further comprising a control unit;
    wherein the control unit comprises a voltage source that is configured to apply a predetermined level of voltage across the first electrode and the second electrode; and
    wherein the control unit comprises an amp meter that is configured to detect current flowing between the first electrode and the second electrode.

5. The system according to claim 4, wherein the control unit comprises an amp meter that is configured to detect a level of current flowing between the first electrode and the second electrode; and
    wherein the control unit is configured to determine whether the detected current level between the first electrode and the second electrode exceeds a threshold current level.

6. The system according to claim 5, wherein the first electrode, the second electrode, and the control unit are configured such that when the insulator coating comprises a desired level of coverage over the surface of the turbine rotor blade, the predetermined voltage level applied across the first electrode and the second electrode fails to induce the detected current level between the first electrode and the second electrode to exceed the threshold current level.

7. The system according to claim 5, wherein the first electrode, the second electrode, and the control unit are configured such that:
    during a first operating condition, the detected current level between the first electrode and the second electrode does not exceed the threshold current level; and
    during a second operating condition, the detected current level between the first electrode and the second electrode exceeds the threshold current level;
    wherein the second operating condition comprises an operating conditioning in which a defect is present in the insulator coating.

8. The system according to claim 7, wherein the defect comprises an exposed area of a predetermined size on the turbine rotor blade, the exposed area comprising an area that is substantially no longer covered by the insulator coating; and
    wherein the predetermined size of the exposed area corresponds to an area of exposure at which the predetermined voltage level induces the detected current level to exceed the threshold current level.

9. The system according to claim 7, wherein the defect comprises one of spallation of the insulator coating and crack formation within the turbine rotor blade.

10. The system according to claim 7, wherein the first operating condition comprises an operating condition in which a desired portion of the surface of the turbine rotor blade that would be exposed to the hot-gas flowpath of the combustion turbine engine is covered by the insulator coating; and
    wherein the control unit is configured to issue a warning notification when the second operating condition occurs.

11. The system according to claim 10, wherein:
    the insulator coating comprises an electrical conductivity that is less than the electrical conductivity of the turbine rotor blade;
    the insulator coating comprises an electrical conductivity that is less than the approximate electrical conductivity of the hot-gas flowpath during operation between the turbine rotor blade and the second electrode; and the desired portion comprises substantially all of the surface area of the turbine rotor blade that would be exposed to the hot-gas flowpath of the combustion turbine engine.

12. The system according to claim 1, wherein, during operation, the hot-gas flowpath of the combustion turbine engine comprises an electrically conductive doping agent; and
wherein the electrically conductive doping agent is injected into the hot-gas flowpath at predetermined testing intervals.

13. A method for detecting defects in a turbine rotor blade of a combustion turbine engine while the combustion turbine engine is operating, the method comprising the steps of:
providing a first electrode that is electrically connected to the turbine rotor blade;
providing a second electrode that resides in proximity to the turbine rotor blade;
applying a voltage across the first electrode and the second electrode; and
detecting current flowing between the first electrode and the second electrode.

14. The method according to claim 13, further comprising the steps of coating the turbine rotor blade with an insulator coating;
wherein:
the insulator coating comprises an electrical conductivity that is less than the electrical conductivity of the turbine rotor blade; and
the insulator coating comprises an electrical conductivity that is less than the approximate electrical conductivity of the combustion gases of hot-gas flowpath between the turbine rotor blade and the second electrode during operation of the combustion turbine engine.

15. The method according to claim 14, wherein the second electrode is connected to stationary structure just downstream of a row of turbine blades in which the turbine rotor blade is included; and
wherein the second electrode is positioned such that the second electrode is exposed to the combustion gases of the hot-gas flowpath during operation of the combustion turbine engine.

16. The method according to claim 14, further comprising the steps of:
detecting a level of current flowing between the first electrode and the second electrode; and
determining whether the detected current level exceeds a threshold current level.

17. The method according to claim 16, wherein the threshold current level corresponds to a threshold above which detected current levels comprise a high probability of being caused by a defect in the insulator coating.

18. The method according to claim 17, wherein the defect comprises an exposed area of predetermined size on the turbine rotor blade, the exposed area comprising an area that is substantially no longer covered by the insulator coating; and
wherein the predetermined size of the exposed area corresponds to a size at which the predetermined voltage level induces the detected current level to exceed the threshold current level.

19. The method according to claim 17, wherein detected current levels that do not exceed the threshold current level correspond to current levels that occur when a desired portion of the surface area of the turbine rotor blade that would be exposed to the combustion gases of the hot-gas flowpath remains covered by the insulator coating;
further comprising the step of issuing a warning notification when the detected current level exceeds the threshold current level.

20. The method according to claim 13, further comprising the step of injecting an electrically conductive doping agent into the hot-gas flowpath at a position in the hot-gas flowpath that is upstream from the turbine rotor blade.

21. The method according the claim 20, wherein the electrically conductive doping agent is configured to increase the electrical conductivity of the combustion gases flowing through the hot-gas flowpath during operation of the combustion turbine engine.

22. The method according to claim 21, wherein the electrically conductive doping agent is injected periodically, the periods of injection corresponding to a desired testing schedule.

* * * * *